US00PP36034P2

(12) United States Plant Patent
Hansen

(10) Patent No.: US PP36,034 P2
(45) Date of Patent: Jul. 23, 2024

(54) ***COREOPISIS* PLANT NAMED 'Golden Needles'**

(50) Latin Name: *Coreopsis verticillata*
Varietal Denomination: Golden Needles

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,665

(22) Filed: Dec. 15, 2023

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
CPC ..... A01H 6/14
See application file for complete search history.

*Primary Examiner* — Keith O. Robinson

(57) ABSTRACT

A new and distinct Threadleaf *Coreopsis* plant, *Coreopsis verticillata* plant named 'Golden Needles', with narrowly-linear, deeply-dissected, typically 3-lobed up to 6-lobed foliage of bright-green, numerous flowers of golden-yellow ray florets with a small, well-defined, maroon center over a prolonged flowering season from mid-June until late summer. The new plant is useful for landscaping as a specimen plant, en masse, in containers, and as a cut flower.

1 Drawing Sheet

Botanical designation: *Coreopsis verticillata.*
Cultivar denomination: 'Golden Needles'.

STATEMENT REGARDING PRIOR DISCLOSURES UNDER 37 CFR 1.77(B)(6)

The first public disclosure of 'Golden Needles', in the form of a website to the public and email release to customers, was made by Walters Gardens, Inc. on Dec. 1, 2023. Walters Gardens, Inc. obtained the new plant and information about the new plant directly from the inventor. The first offer for sale of the new plant was on Jan. 9, 2023, by Walters Gardens, Inc. No plants of *Coreopsis* 'Golden Needles' have been offered for sale or sold, in this country or anywhere in the world, nor has any disclosure of the new plant been made, more than one year prior to the filing date of this application, and such sale or disclosure within one year was either derived directly or indirectly from the inventor.

BACKGROUND OF THE PLANT

The present invention relates to the new and distinct Threadleaf *Coreopsis* herein also referred to as *Coreopsis* 'Golden Needles', by the cultivar name, 'Golden Needles', or as the new plant. The new plant was initially selected by the inventor from a cross on Jul. 24, 2018 between the unnamed proprietary hybrid plant identified by breeder code 17-11-2 (not patented) as the female parent crossed with 'Zagreb' (not patented) in the research facility of a wholesale perennial nursery based in Zeeland, MI, USA. The single seedling identified by breeder code 18-6-6 was then isolated and compared in subsequent years to other *Coreopsis* and subsequently found to be different from all cultivars known to the discoverer. In the evaluation process, the new plant was assigned the breeder code 18-6-6.

Asexual propagation at the same nursery in Zeeland, MI, USA by cuttings has shown 'Golden Needles' to be stable and reproduce true to type in successive generations since spring 2019.

SUMMARY OF THE PLANT

*Coreopsis* 'Golden Needles' has not been observed in all possible environmental conditions. The phenotype may vary slightly with changes in environments such as light intensity, fertility, water availability, etc. without, however any variation in genotype.

*Coreopsis* 'Golden Needles' is distinct from all cultivars known to the inventor in the following traits:

1. Narrow foliage with compact height and dense habit.
2. Heavy flowering of golden-yellow ray florets with sharp, well-defined, maroon centers.
3. The flowers are produced tightly and densely above the bright-green thin foliage.
4. Long flowering period beginning with concentration in mid-June and continuing until late summer.

Plants of *Coreopsis* 'Golden Needles' are most similar to: 'Curry Up' U.S. Plant Pat. No. 28,521, 'Red Hot Vanilla' U.S. Plant patent Application Ser. No. 16/350,350, 'Route 66' U.S. Plant Pat. No. 20,609, 'Electric Avenue' U.S. Plant Pat. No. 24,688, 'Broad Street' U.S. Plant Pat. No. 24,598 and 'Red Chiffon' U.S. Plant Pat. No. 27,528.

'Curry Up' has ray florets that are deeper reddish on the inside and the apices are more narrowly acute. 'Red Hot Vanilla' has ray florets that are cream-colored on the outside and dark red in the center. 'Route 66' has ray florets that are paler yellow on the outside and lighter reddish in the center with flecking toward the apex. 'Electric Avenue' has ray florets that are a solid yellow without the dark red center. 'Broad Street' has lighter reddish ray florets with just a speckling of the yellow toward the apices. 'Red Chiffon' has ray florets that are also paler yellow on the outside and the eye is larger stretching near the apices.

The female has darker gold ray florets and the reddish center was larger, and the male parent has solid yellow ray florets.

BRIEF DESCRIPTION OF THE DRAWINGS

The color drawings illustrate the overall characteristics of *Coreopsis* 'Golden Needles' as three-year-old plants grown in a full-sun trial garden in Zeeland, Michigan. The colors are as true as reasonably possible given the technology available. The color values may vary slightly depending on light intensity and quality.

DETAILED BOTANICAL DESCRIPTION

Figure 1:
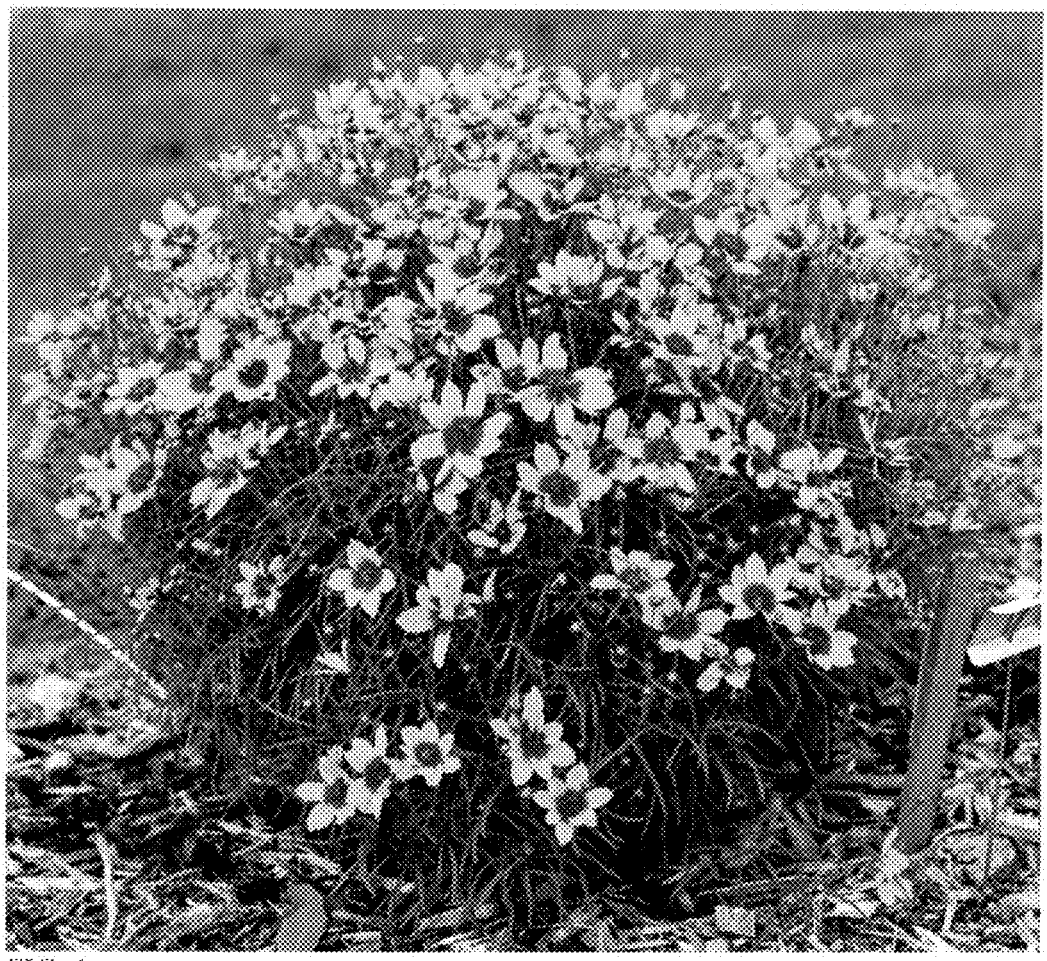
FIG. 1 shows three new plants in a landscape environment.
Figure 2:
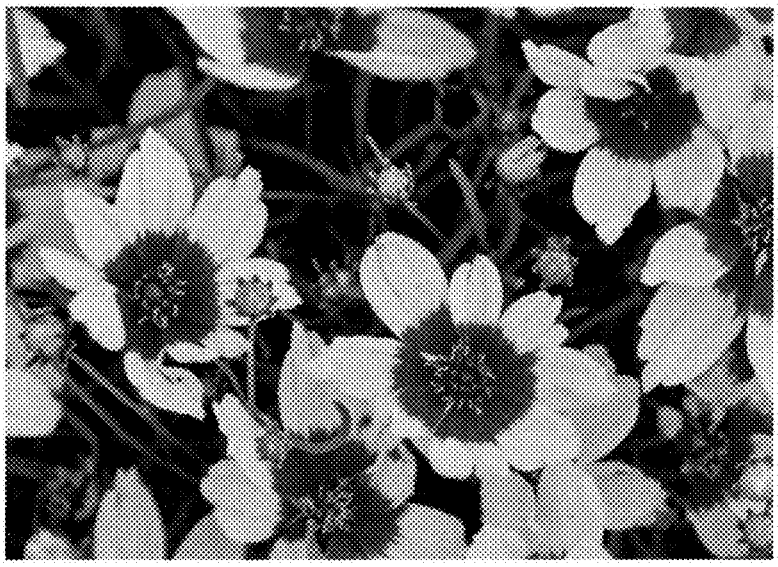
FIG. 2 shows a close-up of the flowers of the new plant.

The following description is based on a three-year-old plant growing in a full-sun trial garden in Zeeland, MI, USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent 17-11-2; male or pollen parent was 'Zagreb';

Asexual propagation: Cuttings, about 10 to 14 days to initiate roots; time to finish as #1 field grown size about 9 months;

Plant habit: Dense axillary branches; rounded, herbaceous perennial mound; up to 48 cm wide and 40 cm tall; average about 45 cm across and 39 cm tall;

Branches: Up to 8 per stem, lower branches compound; glabrous, cylindrical; to 34 cm long and 4 mm diameter; emerging at an angle about 55 degrees above horizontal;

Branch color: Nearest RHS 146B;

Leaves: Opposite; entire; variable, linear to irregularly tri-lobed, or penta-lobed, or hepta-lobed, deeply dissected to midrib; acute apex; base attenuate; sessile; glabrous;

Leaf size: Up to 7 cm long and 8.5 cm wide, average about 5 cm long and 4.5 cm wide; side lobes at about a 45° to 75° angle to center lobe, side lobes to 4.8 cm long and 2 mm across; center lobe to 39 mm long and 2 mm wide;

Leaf color: Young expanding leaves adaxial nearest RHS 137B and abaxial between RHS 146A and RHS 146B; mature leaves adaxial between RHS 137A and RHS 137B, abaxial between RHS 137B and RHS 147B;

Veins: Pinnate; only abaxial midrib obvious;

Midrib color: Adaxial nearest RHS 137A, abaxial nearest RHS 137B;

Inflorescence: Radiate; composite consisting of ray and disk florets; on terminal branches; about 3.6 cm diameter, about 1.2 cm tall from lower involucral bracts to top of disk florets; attitude upright to outwardly; to about 120 inflorescences per stem and 800 inflorescences per plant;

Flower fragrance: None detected;

Phyllary: Two distinct whorls; an outer or lower set consisting of about eight, salient, glabrous adaxial and abaxial, with acute apex, lanceolate, truncate base, to about 4 mm long and 1 mm wide at base; an inner or upper set pressed tight against ray florets and fused in base to form cup, usually eight in number, to about 6 mm long and about 3 mm wide, ovate, acute apex and rounded base;

Phyllary color: Lower set between RHS NN137B and RHS 137A both adaxial and abaxial; upper set between RHS 137A and RHS 146A in the proximal and central portion of both adaxial and abaxial, marginally and distally nearest RHS N144A both adaxial and abaxial;

Flowering period: Early summer until late summer, for about 10 weeks;

Flower longevity: 4 to 6 days on the plant or as a cut flower;

Flower buds: One to two days before ray floret flattening — terete; flat top and rounded base; 8 mm wide and 20 mm tall;

Flower bud color: Exposed ray florets nearest RHS 5A with a slight undertone of nearest RHS N144A;

Peduncle: Cylindrical; glabrous; upright attitude; thin, wiry, stiff, strong; to about 0.7 mm diameter at the base and about 6.4 cm long before capitulum;

Peduncle color: Nearest RHS 137B;

Stem: Cylindrical; lightly fluted; highly branched; about ten nodes, average internode spacing about 3 cm; spacing increasing distally; nodes same color as surround stem;

Stem color: Proximally nearest RHS 164B striated with nearest RHS 146B, distally nearest RHS 164B;

Nodes: Swollen to about 6 mm across;

Node color: Same as surrounding stem, distally nearest RHS 164B, proximally nearest RHS 164B;

Ray florets: Imperfect; sterile; zygomorphic; typically, 7 to 8 per inflorescence;

Ray floret ligule: Oblong elongate; glabrous adaxial and adaxial; apex typically two-notched; margin entire; base claw, narrowly cuneate to attenuate; opening flat to form 180° angle with other ray florets; parallel-veined; to about 16 mm long and about 8 mm wide with the basal eye about 4 mm long; basal corolla claw about 1 mm long and about 0.7 mm diameter;

Ray floret color: Adaxial basal 1 mm nearest RHS 1B, 4 mm center eye between RHS 183A and RHS 185A, distally nearest RHS 7A shortly after opening flat and nearest RHS 14A at maturity; abaxial basal 1 mm nearest RHS 1B, distal 15 mm nearest RHS 7A in maturity and nearest RHS 5B when first flat with the proximal 4 mm having a faint undertone of nearest RHS 183A;

Disk florets: About 32 per capitulum; consisting of fused tepals, staminal tube, and pistil; size about 6 mm long by 2 mm wide at apex and about 0.7 mm diameter at base;

*Tepals*.—Four; 3 mm long and 1 mm wide, corolla fused in the basal 2 mm, acute apex.

*Tepal color*.—Adaxial between RHS 175A and RHS 175B in distal free 1 mm, abaxial distal 1 mm nearest RHS 175A, and basal 2 mm nearest RHS 153D.

*Staminal tube*.—Made up of four fused stamens, about 3 mm long.

*Anther*.—Fused; about 2 mm long and 0.5 mm diameter, nearest RHS N186A.

*Filament*.—Four; cylindrical; about 1 mm long and 0.1 mm diameter; color nearest RHS 4A.

*Anther*.—Fused; about 2 mm long and 0.5 mm diameter, nearest RHS N186A.

*Pollen*.—Fine, round, closest to RHS 17A.

*Style*.—Cylindrical; about 5 mm long and 0.2 mm diameter; nearest RHS 14C below stigma and transitioning to nearest RHS 1C at base.

*Stigma*.—Bifid and cochleate as it matures; about 1 mm long and 0.3 mm diameter color nearest RHS 17B.

Seed: Linear, flattened, slightly arcuate; with rounded apex and rounded base; margins micro-erose; about 5 mm long, about 2.5 mm across in middle, and about 0.5 mm thick;

Seed color: Variable, between RHS 200A and RHS 202A;

*Coreopsis verticillata* 'Golden Needles' is tolerant of winter temperatures as low as −20° C. and summer temperatures as high as 40° C. Once established it is also tolerant of dry summer conditions but does best with ample moisture and good drainage. It is not known to be tolerant or susceptible to diseases and pests that are common to other *Coreopsis* cultivars.

I claim:

1. A new and distinct cultivar of *Coreopsis* plant named 'Golden Needles' as described and illustrated.

* * * * *